United States Patent [19]

Scopelianos et al.

[11] Patent Number: 5,411,554
[45] Date of Patent: May 2, 1995

[54] LIQUID POLYMER FILLED ENVELOPES FOR USE AS SURGICAL IMPLANTS

[75] Inventors: Angelo G. Scopelianos; Rao S. Bezwada, both of Whitehouse Station; Stephen C. Arnold, Franklin, all of N.J.; Richard D. Gooding, Easton, Pa.

[73] Assignee: Ethicon, Inc., Somerville, N.J.

[21] Appl. No.: 95,129

[22] Filed: Jul. 20, 1993

[51] Int. Cl.$^6$ .............................................. A61F 2/12
[52] U.S. Cl. ............................................ 623/8; 623/7; 128/898
[58] Field of Search ............. 623/7, 8; 604/890.1; 128/898

[56] References Cited

U.S. PATENT DOCUMENTS

| | | |
|---|---|---|
| 4,298,998 | 11/1981 | Naficy . |
| 4,657,553 | 4/1987 | Taylor . |
| 4,740,208 | 4/1988 | Cavon . |
| 4,772,284 | 9/1988 | Jefferies et al. . |
| 4,772,285 | 9/1988 | Ksander et al. . |
| 4,936,858 | 7/1990 | O'Keeffe . |
| 4,995,882 | 2/1991 | Destouet et al. . |
| 5,061,281 | 10/1991 | Mares et al. . |
| 5,116,371 | 5/1992 | Christensen et al. ............ 623/8 |
| 5,282,857 | 2/1994 | Perry et al. ............ 623/8 |

OTHER PUBLICATIONS

J. Heller, et al., "Controlled Drug Release from Bioerodible Hydrophobic Ointments", Biomaterials, May 1990, vol. 11, pp. 235–237.

*Primary Examiner*—Paul Prebilic
*Attorney, Agent, or Firm*—Hal Brent Woodrow

[57] ABSTRACT

A cosmetic or prosthetic surgical implant comprising an envelope filled with a liquid bioabsorbable polymer and a process for implanting a cosmetic or prosthetic surgical implant involving the filling of an envelope with a liquid bioabsorbable polymer suitable liquid bioabsorbable polymer include lactone copolymers composed of at least two monomers selected from the group consisting of glycolide, L-lactide, D,L-lactide, 1,4-dioxanone, ε-caprolactone, 1,5-dioxepan-2-one and trimethylene carbonate and poly(orthoesters) of the formula:

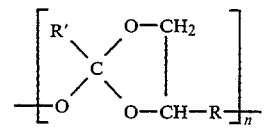

where R is a linear or branched alkylene group containing 3 to 10 carbon atoms and R' is a linear or branched alkyl group containing 1 to 10 carbon atoms and n is selected to provide a liquid poly(orthester) at body temperature.

9 Claims, 1 Drawing Sheet

LIQUID POLYMER FILLED ENVELOPES FOR USE AS SURGICAL IMPLANTS

FIELD OF INVENTION

This invention relates to liquid filled envelopes for use as cosmetic or prosthetic surgical implants.

BACKGROUND OF THE INVENTION

It is estimated that over two million women have had breast implants since their introduction in the mid-60's. Specifically, in 1990, over 132,000 women in the U.S. alone underwent this surgical procedure. Reconstructive surgery following mastectomy or trauma accounts for many of the implant operations, while the remainder of the implant operations were performed to enlarge or reshape the breasts.

Three common types of breast implant devices have been marketed in the U.S.:
  Silicone envelope filled with silicone gel. This is the most frequently implanted product.
  Silicone envelope filled with saline.
  A double lumen implant consisting of an inner silicone envelope filled with silicone gel and an outer envelope that is filled with saline.

The surface of the devices may be either smooth or textured. The textured surface is a silicone or a polyurethane foam coating which is no longer marketed in the U.S. since it was found to degrade and release a known carcinogen in animals.

In 1988, based on increasing safety concerns, the FDA informed manufacturers of the agency's intention to request PMA submission for these products. A Jul. 9, 1991 deadline was set for the manufacturers of silicone gel-filled breast implants to submit data. The manufacturers of saline-filled implants were also advised that they would be required to submit data at a later date. Assisted by the advice of an outside advisory panel, on Jan. 6, 1992, the agency placed a moratorium on the distribution of silicone filled implants.

The moratorium was based on reports implicating the implants with problems such as bleeding, infection, capsular contracture, calcium deposition, rupture, local neurosensory changes, interference with mammography, autoimmune or connection tissue diseases and risk of cancer.

Thus, it would be a significant contribution to the medical device art to provide a cosmetic or prosthetic implant device that does not utilize a silicone gel.

It is an object of the present invention to provide a new medical device comprising an envelope filled with a bioabsorbable liquid.

SUMMARY OF THE INVENTION

We have discovered a cosmetic or prosthetic surgical implant comprising an envelope filled with a liquid bioabsorbable polymer selected from the group consisting of lactone copolymers and polyorthoesters.

We have also discovered a process for manufacturing a cosmetic or prosthetic surgical implant comprising the filling an envelope with a liquid bioabsorbable polymer.

DETAILED DESCRIPTION OF THE INVENTION

Figure 1:
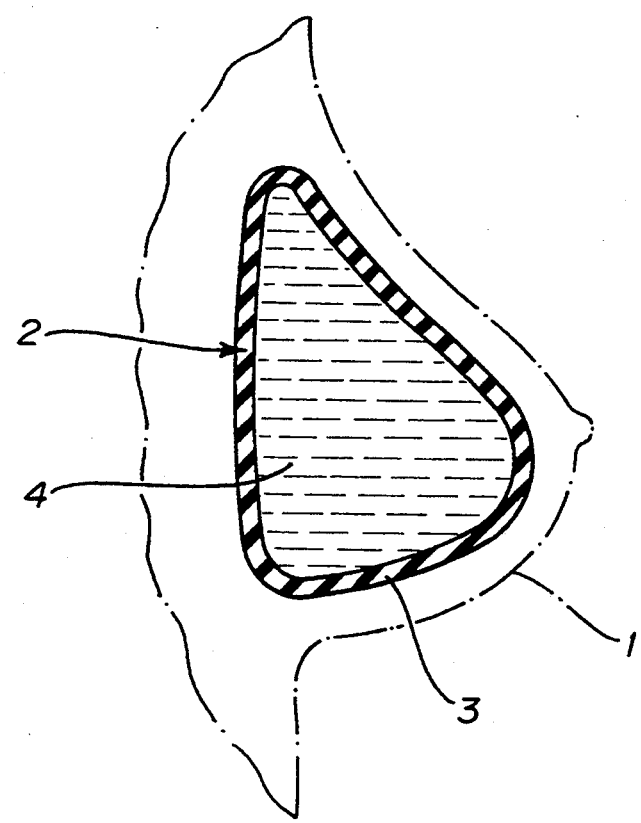
FIG. 1 is a partial section through a female human breast showing the present invention.

The cosmetic or prosthetic surgical implants of this invention are designed to be compatible with soft tissue such as breast tissue. Typical soft tissue implants consist of a core surrounded by a nonabsorbable envelope or lumen. The envelope is generally made from a single or multiple layer film consisting in part of a flexible, water impermeable material such as implantable silicon rubbers, polyurethanes or polyolefins. The improvement provided by the present invention is that the core or filler used in the implant is an absorbable, nontoxic, liquid polymer.

In FIG. 1, thee is shown a partial section of a human female breast 1 with a breast prosthesis 2 implanted therein. The breast prosthesis 2 has a container or envelope 3 and a core 4 of filling material.

Many nontoxic bioabsorbable homopolymers, copolymers and terpolymers, that are fluids at body temperature, may be used as the filling material for cosmetic or prosthetic implants. In particular, there are many lactone copolymers (which contains two or more comonomers) composed of glycolide, L-lactide, D,L-lactide, 1,4-dioxanone, ε-caprolactone, 1,5-dioxepan-2-one, trimethylene carbonate and other commonly used lactone monomers that are fluids at body temperature. These polymers may be linear, branched, or star branched; statistically random copolymers or terpolymers; segmented block copolymers or terpolymers. Examples of suitable terpolymers are terpolymers containing comonomer combinations selected from the group consisting of glycolide, L-lactide, and p-dioxanone; glycolide, ε-caprolactone and p-dioxanone; and L-lactide, ε-caprolactone and p-dioxanone. These polymers should be purified to remove unreacted monomer which may cause an inflammatory reaction in tissue.

Another class of polymers that may also be used as the filling material are nontoxic bioabsorbable polyorthoesters that are liquids at body temperature. Nontoxic polyorthoesters are described in an article entitled "Controlled Drug Release from Bioerodible Hydrophobic Ointments", by J. Heller et al. in *Biomaterials* 1990, Vol. 11, May, on pages 235–237 (the text of which is hereby incorporated by reference). Suitable polyorthoesters would have the following formula:

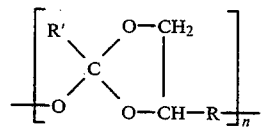

where R is a linear or branched alkylene group containing 3 to 10 carbon atoms and n is selected to provide a liquid at body temperature, R' is a linear or branched alkyl group containing 1 to 10 carbon atoms.

Preferred polymers for use as the filling material for the cosmetic or prosthesis surgical implants are lactone polymers selected from the group consisting of poly(lactide-co-ε-caprolactone), poly(lactide-co-p-dioxanone), poly(lactide-co-1,5-dioxepan-2-one), poly(ε-caprolactone-co-p-dioxanone) and poly(1,5-dioxepan-2-one-co-p-dioxanone). The comonomer ratios of these copolymers should be in the range of from about 70:30 mole percent to about 30:70 mole percent and preferably in the range of from 40:60 mole percent to 60:40 mole percent of the first monomer to second monomer. Most preferably these polymers will be random copolymers.

The viscosity of the polymer should be suitable to provide a prosthesis that as closely as is possible mimic the characteristics of the tissue in which the implant is to be placed. A suitable inherent viscosity for breast implants should be in the range of from about 0.1 dL/g to about 1.2 dL/g, preferably from about 0.1 dL/g to about 0.8 dL/g and most preferably from 0.2 dL/g to 0.5 dL/g, as determined in a 0.1 g/dL solution at 25° C. in hexafluoroisopropanol (HFIP).

Lactone copolymers with suitable inherent viscosity can be formed by polymerizing the monomers with a mono- or difunctional initiator to obtain a linear copolymer having a suitable molecular weight. Alternatively, a multifunctional initiator can be employed to generate a branched or star branched absorbable lactone copolymer. A low viscosity, linear or branched lactone copolymer also can be crosslinked by a variety of methods to provide a copolymer with a suitable viscosity.

For breast implants, it is preferred that the polymers used in these prosthetic devices have a slow rate of hydrolysis in the event that the envelope develops a leak. The slow rate of hydrolysis would allow the prosthetic surgical implant to retain its original viscosity for a prolonged period and minimize the need for immediate replacement of the device. Additionally, since the polymers used as filler material are bioabsorbable, leakage of the filler material should not pose a significant health risk.

Suitable designs for soft allopathic surgical implants are well known in the art. For example, breast implant designs have been described in U.S. Pat. Nos. 4,772,285, 4,298,998, 3,934,274 and 3,293,663 which are hereby incorporated by reference. Preferred breast implant designs for use in the present invention are multiple lumen designs (an outer sac filled with an absorbable polymer or saline solution and an inner sac filled with an absorbable polymer). Also preferred are designs that use single or multiple external coatings or layers to minimize both encapsulation of the breast implant by a fibrous layer of connective tissue and penetration of moisture into the inner sac.

The following Examples are provided to further illustrate, but in no way limit, the scope of the claimed invention.

EXAMPLE 1

Copolymerization of ε-Caprolactone and p-Dioxanone 60:40 (mol/mol) ε-Caprolactone:p-Dioxanone Initial Composition A flame dried, 250 mL, single neck round bottom flask was charged with 68.5 grams (600 mmol) of vacuum distilled ε-caprolactone, 40.8 (400 mmol) of p-dioxanone, 3.7 milliliters (49 mmol) of propylene glycol (USP grade), and 0.12 milliliters (40 μmol) of a 0.33M stannous octoate solution in toluene. The flask was fitted with a flame dried mechanical stirrer. The reactor flask was flushed with dry nitrogen gas, and an inert atmosphere was maintained throughout the reaction. The reaction mixture was heated to 160° C. for 24 hours, and then, the reaction temperature was reduced to 110° C. and held there for about 24 hours. The copolymer was a viscous liquid at room temperature and was vacuum dried at 80° C. for about 80 hours (0.1 mm Hg) to remove any unreacted monomers. The copolymer had an inherent viscosity of 0.19 dL/g in hexafluoroisopropanol (HFIP) at 25° C. (c=0.10 g/dL). The liquid copolymer exhibited a Brookfield viscosity of 7,620 cps at 25° C. The weight average molecular weight ($M_w$) was 3230 daltons and the number average molecular weight ($M_n$) was 1990 daltons as determined by gel permeation chromatography (GPC) using polymethacrylate standards. The copolymer composition was measured by 300 MHz $^1$H NMR spectroscopy and found the repeating units to be 64.6 mole percent poly[ε-caprolactone] and 32.6 mole percent poly[p-dioxanone] with a 2.8 mole percent residue of p-dioxanone monomer.

EXAMPLE 2

Copolymerization of ε-Caprolactone and p-Dioxanone 50:50 (mol/mol) ε-Caprolactone:p-Dioxanone Initial Composition The procedure of Example 1 was essentially repeated except that the reaction flask was charged with 57.0 grams (500 mmol) of vacuum distilled ε-caprolactone, 51.0 grams (500 mmol) of p-dioxanone, 3.7 milliliters (49 mmol) of propylene glycol (USP grade), and 0.12 milliliters (40 μmol) of a 0.33M stannous octoate solution in toluene. Moreover, the reaction temperature scheme was different: the polymerization was conducted at 140° C. for 24 hours. The copolymer was a viscous liquid at room temperature and had an inherent viscosity of 0.22 dL/g in HFIP at 25° C. (c=0.10 g/dL). The copolymer had a Brookfield viscosity of 11,200 cps at 25° C. The $M_w$ was 3290 daltons and the $M_n$ was 1850 daltons as determined by GPC.

EXAMPLE 3

Copolymerization of ε-Caprolactone and p-Dioxanone 40:60 (mol/mol) ε-Caprolactone:p-Dioxanone Initial Composition The procedure of Example 1 was essentially repeated except that the reaction flask was charged with 45.7 grams (400 mmol) of vacuum distilled ε-caprolactone, 61.3 grams (600 mmol) of p-dioxanone, 3.7 milliliters (49 mmol) of propylene glycol (USP grade), and 0.12 milliliters (40 μmol) of a 0.33M stannous octoate solution in toluene. The copolymer was a viscous liquid at room temperature and had an inherent viscosity of 0.18 dL/g in HFIP at 25° C. (c=0.10 g/dL). This copolymer had a Brookfield viscosity of 11,700 cps at 25° C. The $M_w$ was 2960 daltons and the $M_n$ was 1720 daltons as determined by GPC. The copolymer composition was measured by 300 MHz $^1$H NMR spectroscopy. The copolymer was composed of 48.8 mole percent poly[ε-caprolactone] and 47.8 mole percent poly[p-dioxanone] repeating units and 3.4 mole percent residual p-dioxanone monomer.

EXAMPLE 4

Copolymerization of ε-Caprolactone and p-Dioxanone 50:50 (mol/mol) ε-Caprolactone:p-Dioxanone Initial Composition The procedure of Example 2 was repeated except that 0.74 milliliters (9.7 mmol) of propylene glycol (USP grade) were used instead of 3.7 milliliters to obtain a copolymer with a higher molecular weight. The resulting copolymer was a liquid at room temperature and had an inherent viscosity of 0.46 dL/g in HFIP at 25° C. (c=0.10 g/dL). The copolymer composition was measured by 300 MHz $^1$H NMR spectroscopy and found to be 51.9 mole percent poly[ε-caprolactone] and 48.1 mole percent poly[p-dioxanone] repeating units.

EXAMPLE 5

Copolymerization of ε-Caprolactone and p-Dioxanone 50:50 (mol/mol) ε-Caprolactone:p-Dioxanone Initial Composition The procedure of Example 2 was repeated except that 0.57 milliliters (7.5 mmol) of propylene glycol (USP grade) were used instead of 3.7 milliliters to obtain a copolymer with a higher molecular weight. The resulting copolymer was a liquid at room temperature and had an inherent viscosity of 0.73 dL/g in HFIP at 25° C. (c=0.10 g/dL). The copolymer composition was determined by 300 MHz $^1$H NMR spectroscopy. The copolymer was composed of 54.8 mole percent poly[ε-caprolactone] and 42.5 mole percent poly[p-dioxanone] repeating units and 2.7 mole percent residual p-dioxanone monomer.

EXAMPLE 6

Copolymerization of ε-Caprolactone and p-Dioxanone 50:50 (mol/mol) ε-Caprolactone:p-Dioxanone Initial Composition The procedure of Example 2 was repeated except that 0.19 milliliters (2.5 mmol) of propylene glycol (USP grade) were used instead of 3.7 milliliters to obtain a copolymer with a higher molecular weight. The resulting copolymer had an inherent viscosity of 1.3 dL/g in HFIP at 25° C. (c=0.10 g/dL).

EXAMPLE 7

Copolymerization of ε-Caprolactone and p-Dioxanone 70:30 (mol/mol) ε-Caprolactone:p-Dioxanone Initial Composition A flame dried, 250 mL, single neck round bottom flask was charged with 79.9 grams (700 mmol) of vacuum distilled ε-caprolactone, 30.6 (300 mmol) of p-dioxanone, 0.73 milliliters (9.6 mmol) of propylene glycol (USP grade), and 0.12 milliliters (40 μmol) of a 0.33M stannous octoate solution in toluene. The flask was fitted with a flame dried mechanical stirrer. The reactor flask was flushed with dry nitrogen gas, and an inert atmosphere was maintained throughout the reaction. The reaction mixture was heated to 160° C. for 24 hours, and then, the reaction temperature was reduced 110° C. and held there for about 24 hours. The copolymer was a viscous liquid at room temperature and was vacuum dried at 80° C. for about 80 hours (0.1 mm Hg) to remove any unreacted monomers. The copolymer had an inherent viscosity of 0.53 dL/g HFIP at 25° C. (c=0.10 g/dL). The copolymer composition was measured by 300 MHz $^1$H NMR spectroscopy. The copolymer was found to be composed of 70.8 mole percent poly[ε-caprolactone] and 26.8 mole percent poly[p-dioxanone] repeating units and contained a 2.4 mole percent residue of p-dioxanone monomer.

EXAMPLE 8

Copolymerization of ε-Caprolactone and p-Dioxanone 65:35 (mol/mol) ε-Caprolactone:p-Dioxanone Initial Composition The procedure of Example 1 was essentially repeated except that the reaction flask was charged with 74.2 grams (650 mmol) of vacuum distilled ε-caprolactone, 35.7 grams (350 mmol) of p-dioxanone, 0.73 milliters (9.6 mmol) of propylene glycol (USP grade), and 0.12 milliliters (40 μmol) of a 0.33M stannous octoate solution in toluene. The copolymer was a viscous liquid at room temperature and had an inherent viscosity of 0.56 dL/g in HFIP at 25° C. (c=0.10 g/dL). The copolymer composition was measured by 300 MHz $^1$H NMR spectroscopy. The copolymer was composed of 67.3 mole percent poly[ε-caprolactone] and 30.5 mole percent poly[p-dioxanone] repeating units and contained a 2.2 mole percent residue of p-dioxanone monomer.

EXAMPLE 9

Copolymerization of ε-Caprolactone and p-Dioxanone 35:65 (mol/mol) ε-Caprolactone:p-Dioxanone Initial Composition The procedure of Example 1 was essentially repeated except that the reaction flask was charged with 40.0 grams (350 mmol) of vacuum distilled ε-caprolactone, 66.4 grams (650 mmol) of p-dioxanone, 0.73 milliliters (9.6 mmol) of propylene glycol (USP grade), and 0.12 milliliters (40 μmol) of a 0.33M stannous octoate solution in toluene. The copolymer was a viscous liquid at room temperature and had an inherent viscosity of 0.49 dL/g in HFIP at 25° C. (c=0.10 g/dL). The copolymer composition was measured by 300 MHz $^1$H NMR spectroscopy. The copolymer was found to be 40.4 mole percent poly[ε-caprolactone] and 54.8 mole percent poly[p-dioxanone] repeating units and contained a 4.8 mole percent residue of p-dioxanone monomer.

EXAMPLE 10

Copolymerization of ε-Caprolactone and p-Dioxanone 30:70 (mol/mol) ε-Caprolactone:p-Dioxanone Initial Composition The procedure of Example 1 was essentially repeated except that the reaction flask was charged with 34.2 grams (300 mmol) of vacuum distilled ε-caprolactone, 71.5 grams (700 mmol) of p-dioxanone, 0.73 milliliters (9.6 mmol) of propylene glycol (USP grade), and 0.12 milliliters (40 μmol) of a 0.33M stannous octoate solution in toluene. The copolymer was a viscous liquid at room temperature and had an inherent viscosity of 0.46 dL/g in HFIP at 25° C. (c=0.10 g/dL). The copolymer composition was measured by 300 MHz $^1$H NMR spectroscopy. The copolymer was found to be 36.0 mole percent poly[ε-caprolactone] and 59.3 mole percent poly[p-dioxanone] repeating units and contained a 4.7 mole percent residue of p-dioxanone monomer.

EXAMPLE 11

Copolymerization of ε-Caprolactone and L-Lactide 50:50 (mol/mol) ε-Caprolactone:L-Lactide Initial Composition A flame dried, 250 mL, single neck round bottom flask was charged with 57.1 grams (500 mmol) of vacuum distilled ε-caprolactone, 72.1 (500 mmol) of L-lactide, 3.7 milliliters (49 mmol) of propylene glycol (USP grade), and 0.10 milliliters (33 μmol) of a 0.33M stannous octoate solution in toluene. The flask was fitted with a flame dried mechanical stirrer. The reactor flask was flushed with dry nitrogen gas, and an inert atmosphere was maintained throughout the reaction. The reaction mixture was heated to 160° C. for 20 hours. The copolymer was a viscous liquid at room temperature and was dried under vacuum at 110° C. for 16 hours (0.1 mm Hg) to remove any unreacted monomers. The copolymer had an inherent viscosity of 0.17 dL/g in HFIP at 25° C. (c=0.10 g/dL). The copolymer composition was measured by 300 MHz $^1$H NMR spectroscopy. The copolymer was found to be 53.3 mole percent poly[ε-caprolactone] and 46.7 mole percent poly[L-lactide] repeating units.

EXAMPLE 12

Copolymerization of ε-Caprolactone and L-Lactide 60:40 (mol/mol) ε-Caprolactone:L-Lactide Initial Composition The procedure of Example 11 was essentially repeated except that the reaction flask was charged with 68.1 grams (600 mmol) of vacuum distilled ε-caprolactone and 57.7 (400 mmol) of L-lactide. The copolymer was a viscous liquid at room temperature and was dried under a vacuum at 110° C. for 7 hours (0.1 mm Hg) to remove any unreacted monomers. The copolymer had an inherent viscosity of 0.16 dL/g in HFIP at 25° C. (c=0.10 g/dL). The copolymer composition was measured by 300 MHz $^1$H NMR spectroscopy. The copolymer was found to be 62.9 mole percent poly[ε-caprolactone] and 37.1 mole percent poly[L-lactide] repeating units.

EXAMPLE 13

Copolymerization of ε-Caprolactone and L-Lactide 60:40 (mol/mol) ε-Caprolactone:L-Lactide Initial Composition The procedure of Example 12 was essentially repeated except that 0.74 milliliters (9.7 mmol) of propylene glycol (USP grade) were used instead of 3.7 milliliters to obtain a copolymer of higher molecular weight. The copolymer was a viscous liquid at room temperature and had an inherent viscosity of 0.58 dL/g in HFIP at 25° C. (c=0.10 g/dL). The liquid copolymer composition was measured by 300 MHz $^1$H NMR spectroscopy and found to be 62.9 mole percent poly[ε-caprolactone] repeating units and 37.1 mole percent poly[L-lactide] repeating units.

EXAMPLE 14

Copolymerization of ε-Caprolactone and L-Lactide 70:30 (mol/mol) ε-Caprolactone:L-Laotide Initial Composition The procedure of Example 11 was essentially repeated except that the reaction flask was charged with 79.9 grams (700 mmol) of ε-caprolactone and 43.2 grams (300 mmol) of L-lactide. The copolymer was a viscous liquid at room temperature and had an inherent viscosity of 0.16 dL/g in HFIP at 25° C. (c=0.10 g/dL). The copolymer composition was measured by 300 MHz $^1$H NMR spectroscopy and found to be 70.8 mole percent poly[ε-caprolactone] repeating units and 29.2 mole percent poly[L-lactide] repeating units.

EXAMPLE 15

Copolymerization of ε-Caprolactone and L-Lactide 70:30 (mol/mol) ε-Caprolactone:L-Lactide Initial Composition The procedure of Example 14 was essentially repeated except that 0.74 milliliters (9.7 mmol) of propylene glycol (USP grade) were used instead of 3.7 milliliters to obtain a copolymer of higher molecular weight. The copolymer was a very viscous liquid at room temperature and had an inherent viscosity of 0.55 dL/g in HFIP at 25° C. (c=0.10 g/dL). The copolymer composition was measured by 300 MHz $^1$H NMR spectroscopy and found to be 74.8 mole percent poly[ε-caprolactone] repeating units and 25.2 mole percent poly[L-lactide] repeating units.

EXAMPLE 16

Copolymerization of ε-Caprolactone and L-Lactide 50:50 (mol/mol) ε-Caprolactone:L-Lactide Initial Composition A flame dried, 250 mL, round bottom single neck flask was charged with 57.1 grams (0.50 mole) of ε-caprolactone, 72.1 grams (0.50 mole) of L-lactide, 0.74 milliliters (9.7 mmol) of propylene glycol (USP grade), and 0.10 milliliters (33 μmol) of a 0.33M stannous octoate solution in toluene. The flask was fitted with a flame dried mechanical stirrer. The reactor flask was purged with nitrogen three times before venting with nitrogen. The reaction mixture was heated to 160° C. and maintained at this temperature for about 20 hours. The copolymer was dried under vacuum (0.1 mm Hg) at 110° C. for about 16 hours to remove any unreacted monomers. The copolymer had an inherent viscosity of 0.51 dL/g in HFIP at 25° C. The copolymer was a very viscous liquid at room temperature. The copolymer composition was measured by 300 MHz $^1$H NMR spectroscopy and found to be 49.4 mole percent poly[ε-caprolactone] repeating units and 50.6 mole percent poly[L-lactide] repeating units.

EXAMPLE 17

Copolymerization of ε-Caprolactone and L-Lactide 45:55 (mol/mol) ε-Caprolactone:L-Lactide Initial Composition The procedure in Example 16 was substantially repeated except that 51.4 grams (0.45 mole) of ε-caprolactone, 79.3 grams (0.55 mole) of L-lactide were used. The copolymer was dried under vacuum (0.1 mm Hg) at 110° C. for about 7 hours to remove any unreacted monomers. The copolymer had an inherent viscosity of 0.22 dL/g in HFIP at 25° C. The copolymer was a liquid at room temperature. The copolymer composition was measured by 300 MHz $^1$H NMR spectroscopy and found to be 44.8 mole percent poly[ε-caprolactone] and 50.8 mole percent poly[L-lactide] repeating units. The copolymer also contained 1.2 mole percent residual ε-caprolactone and 3.2 mole percent of propylene glycol esters.

EXAMPLE 18

Copolymerization of ε-Caprolactone and L-Lactide 40:60 (mol/mol) ε-Caprolactone:L-Lactide Initial Composition The procedure in Example 17 was substantially repeated except that 45.7 grams (0.40 mole) of ε-caprolactone, 86.5 grams (0.60 mole) of L-lactide were used. The copolymer was dried under vacuum (0.1 mm Hg) at 110° C. for about 7 hours to remove any unreacted monomers. The copolymer had an inherent viscosity of 0.38 dL/g in HFIP at 25° C. The copolymer was a liquid at room temperature. The copolymer composition was measured by 300 MHz $^1$H NMR spectroscopy and found to be 40.0 mole percent poly[ε-caprolactone] and 54.2 mole percent poly[L-lactide] repeating units. The copolymer also contained 1.9 mole percent residual ε-caprolactone and 3.9 mole percent of propylene glycol esters.

EXAMPLE 19

Copolymerization of ε-Caprolactone and L-Lactide 35:65 (mol/mol) ε-Caprolactone:L-Lactide Initial Composition The procedure in Example 17 was substantially repeated except that 40.0 grams (0.35 mole) of ε-caprolactone, 93.7 g (0.65 mole) of L-lactide were used. The copolymer was dried under vacuum (0.1 mm Hg) at 110° C. for about 7 hours to remove any unreacted monomers. The copolymer had an inherent viscosity of 0.19 dL/g in HFIP at 25° C. The copolymer was a liquid at room temperature. The copolymer composition was measured by 300 MHz $^1$H NMR spectroscopy and found to be 35.6 mole percent poly[ε-caprolactone] and 54.2 mole percent poly[L-lactide] repeating units. The copolymer also contained 1.2 mole percent residual ε-caprolactone and 3.7 mole percent of propylene glycol esters.

EXAMPLE 20

Copolymerization of ε-Caprolactone and L-Lactide 45:55 (mol/mol) ε-Caprolactone:L-Lactide Initial Composition The procedure in Example 16 was substantially repeated except that 6.0 milliliters (82 mmol) of glycerol (USP grade) was used instead of 0.74 milliliters of propylene glycol. The copolymer was dried under vacuum (0.1 mm Hg) at 110° C. for about 7 hours to remove any unreacted monomers. The copolymer had an inherent viscosity of 0.12 dL/g in HFIP at 25° C. The copolymer was a liquid at room temperature. The copolymer composition was measured by 300 MHz $^1$H NMR spectroscopy and found to be 46.5 mole percent poly[ε-caprolactone] and 43.6 mole percent poly[L-lactide] repeating units. The copolymer also contained 2.2 mole percent residual ε-caprolactone and 7.7 mole percent of glycerol esters.

EXAMPLE 21

Copolymerization of ε-Caprolactone and L-Lactide 40:60 (mol/mol) ε-Caprolactone:L-Lactide Initial Composition The procedure in Example 20 was substantially repeated except that 45.7 grams (0.40 mole) of ε-caprolactone, 86.5 grams (0.60 mole) of L-lactide were used. The copolymer was dried under vacuum (0.1 mm Hg) at 110° C. for about 7 hours to remove any unreacted monomers. The copolymer had an inherent viscosity of 0.11 dL/g in HFIP at 25° C. The copolymer was a liquid at room temperature. The copolymer composition was measured by 300 MHz $^1$H NMR spectroscopy and found to be 40.4 mole percent poly[ε-caprolactone] and 49.0 mole percent poly[L-lactide] repeating units. The copolymer also contained 1.7 mole percent residual ε-caprolactone and 8.9 mole percent of glycerol esters.

EXAMPLE 22

Copolymerization of ε-Caprolactone and L-Lactide 35:65 (mol/mol) ε-Caprolactone:L-Lactide Initial Composition The procedure in Example 20 was substantially repeated except that 40.0 grams (0.35 mole) of ε-caprolactone, 93.7 grams (0.65 mole) of L-lactide were used. The copolymer was dried under vacuum (0.1 mm Hg) at 110° C. for about 7 hours to remove any unreacted monomers. The copolymer had an inherent viscosity of 0.12 dL/g in HFIP at 25° C. The copolymer was a liquid at room temperature. The copolymer composition was measured by 300 MHz $^1$H NMR spectroscopy and found to be 36.3 mole percent poly[ε-caprolactone] and 54.5 mole percent poly[L-lactide] repeating units.

The copolymer also contained 1.3 mole percent residual ε-caprolactone and 7.9 mole percent of glycerol esters.

What is claimed is:

1. A surgical implant comprising a water impermeable envelope filled with one or more liquid bioabsorbable polymers selected from the group consisting of lactone copolymers and poly(orthoesters) wherein the lactone copolymers are composed of at least two monomers selected from the group consisting of glycolide, L-lactide, D,L-lactide, 1,4-dioxanone, ε-caprolactone, 1,5-dioxepan-2-one and trimethylene and the poly(orthoesters) are of the formula:

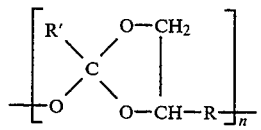

wherein R is a linear or branched alkylene group containing 3 to 10 carbon atoms and R' is a linear or branched alkyl group containing 1 to 10 carbon atoms and n is selected to provide liquid poly(orthoesters) at body temperature.

2. A process for using a surgical implant comprising implanting in a human a sealed envelope filled with a liquid bioabsorbable polymer selected from the group consisting of lactone copolymers and poly(orthoesters), wherein the lactone copolymers are composed of at least two monomers selected from the group consisting of glycolide, L-lactide, D,L-lactide, 1,4-dioxanone, ε-caprolactone, 1,5-dioxepan-2-one and trimethylene carbonate and the poly(orthoesters) are of the formula:

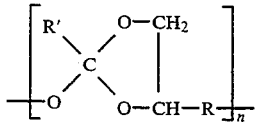

wherein R is a linear or branched alkylene group containing 3 to 10 carbon atoms and R' is a linear or branched alkyl group containing 1 to 10 carbon atoms and n is selected to provide liquid poly(orthoesters) at body temperature.

3. The surgical implant of claim 1 wherein the liquid bioabsorbable polymer is a terpolymer selected from the group consisting of poly(glycolide-co-L-lactide-co-p-dioxanone), poly(glycolide-co-ε-caprolactone-co-p-dioxanone) and poly(L-lactide-co-ε-caprolactone-co-p-dioxanone).

4. The process of claim 2 wherein the liquid bioabsorbable polymer is a terpolymer selected from the group consisting of poly (glycolide-co-L-lactide-co-p-dioxanone), poly(glycolide-co-ε-caprolactone-co-p-dioxanone) and poly(L-lactide-co-ε-caprolactone-co-p-dioxanone).

5. The surgical implant of claim 1 wherein the liquid bioabsorbable polymer is selected from the group consisting of poly(lactide-co-ε-caprolactone), poly(lactide-co-p-dioxanone) and poly(ε-caprolactone-co-p-dioxanone).

6. The process of using the surgical implant of claim 2 further comprising implanting the surgical implant into breast tissue.

7. The surgical implant of claim 1 wherein the envelope is a flexible, water impermeable material selected from the group consisting of silicon rubbers, polyurethanes and polyolefins.

8. The surgical implant of claim 1 wherein the envelope has more than one layer of water impermeable material.

9. The process of claim 2 wherein the liquid bioabsorbable polymer is selected from the group consisting of poly(lactide-co-ε-caprolactone), poly(lactide-co-p-dioxanone), and poly (ε-caprolactone-co-p-dioxanone).

* * * * *